United States Patent [19]

Van Soye et al.

[11] Patent Number: 5,262,066

[45] Date of Patent: Nov. 16, 1993

[54] PROCESS FOR DELIVERING RADIANT ENERGY FOR THE TREATMENT OF FLUIDS

[76] Inventors: Charles C. Van Soye, 3800 Larkstone Dr., Orange, Calif. 92669; John F. Imbalzano, 108 Black Oak Dr., Elkton, Md 21921

[21] Appl. No.: 791,437

[22] Filed: Nov. 13, 1991

[51] Int. Cl.$^5$ .............................. C02F 1/32
[52] U.S. Cl. ...................... 210/748; 204/158.2; 204/158.21; 250/432 R; 250/436; 422/24
[58] Field of Search .............. 210/748, 764; 204/157.15, 158.2, 158.21; 422/22, 23, 24, 186, 186.3; 250/432 R, 435–438

[56] References Cited

U.S. PATENT DOCUMENTS

| | | | |
|---|---|---|---|
| 3,923,663 | 12/1975 | Reid | 210/251 |
| 4,103,167 | 7/1978 | Ellner | 250/432 |
| 4,179,616 | 12/1979 | Coviello et al. | 210/748 |
| 4,276,256 | 6/1981 | Karamian | 250/432 R |
| 4,296,328 | 10/1981 | Regan | 250/436 |
| 4,336,223 | 6/1982 | Hillman | 210/748 |
| 4,467,206 | 8/1984 | Taylor et al. | 250/435 |
| 4,767,932 | 8/1988 | Ellner | 250/435 |
| 4,788,038 | 11/1988 | Matsunaga | 210/748 |
| 4,904,874 | 2/1990 | Ellner | 250/436 |
| 4,968,891 | 11/1990 | Jhawar et al. | 250/436 |

*Primary Examiner*—Neil M. McCarthy

[57] ABSTRACT

A process for treating fluids with ultraviolet radiation effective to destroy microorganisms and to prevent their regrowth is described.

15 Claims, No Drawings

PROCESS FOR DELIVERING RADIANT ENERGY FOR THE TREATMENT OF FLUIDS

FIELD OF THE INVENTION

This invention relates to a process for treating fluids with ultraviolet radiation. More particularly, it relates to a process for treating fluids with ultraviolet radiation effective to destroy viruses, macrophages and microorganisms such as bacteria, molds, protozoa, yeast and algae, and to prevent their regrowth.

BACKGROUND OF THE INVENTION

Fluids, both liquid and gaseous, which are left untreated in pipes and containers, generally develop significant growth of bacteria, viruses and other microorganisms. Such growth occurs in both open systems and in systems which are fully enclosed and where air is excluded. Fully enclosed systems, essentially devoid of oxygen, will generally develop anaerobic growth. Open systems will develop a mixture of aerobic and anaerobic growth. The microorganisms often partition themselves into free-floating groups and may flow through the system or become attached to the walls of the container, tubing or piping. This can result in corrosion of the container, or mechanical blockage of pipes or tubes. In addition, the microbial growth or its subsequent debris can cause product contamination, product failure and disease. Therefore, it is usually desirable to destroy any microorganisms that are present in fluids, and also to prevent new microbial growth.

It is known practice to use chemical treatments to destroy microorganisms in fluids, particularly liquids. For example, chlorination or other halogenation treatments are known to be useful in purifying water. However, with chemical treatments, the amount of chemical required is highly dependent on the level of contamination in the fluid. Using too little chemical results in incomplete destruction of the microorganisms. Using too much chemical can result in contaminating the fluid with the chemical. In addition, such chemicals can be corrosive, deleteriously reactive with other chemicals in the fluid, of environmental concern, or prohibitively expensive.

Nonchemical treatments to destroy microbial growth include exposure to high intensity-ultraviolet light. The fluid generally is exposed through a transparent section of the fluid conduit by an external radiation source. Alternatively, the source can be placed inside the fluid conduit, with appropriate shielding from the fluid when necessary. Such practices can be partially effective in killing unwanted microorganisms in the fluids at the point of application to reduce the number of microorganisms and their associated debris downstream. However, such an approach does nothing to reduce the microbial population upstream from the source, and does not retard the growth of microoranisms which survive the exposure and continue downstream. Furthermore, considerable growth can occur from such microorganisms, especially if the fluid flow is interrupted for any significant amount of time.

It therefore would be desirable to have an improved process for the purification of fluids, and maintenance of high purity fluids, which does not suffer from the above-described disadvantages.

SUMMARY OF THE INVENTION

The present invention provides a process for treating a fluid which comprises exposing the fluid to radiation, said exposure being accomplished by means of (A) (a1) at least one radiation-delivering fiber which transmits, scatters and emits radiation along the length of the fiber, (a2) a multiplicity of radiationdelivering fibers having varying lengths and which emit radiation substantially only at the ends, or (a3) a combination of (a1) and (a2), at least one end of each fiber being connected in a transmitting relationship with (B) a radiation source.

DETAILED DESCRIPTION OF THE INVENTION

The process of the invention can be used to prevent microbial growth from occurring in highly pure fluids. It also can be used to destroy any microbial growth which may have occurred in a less-pure fluid. The process may be used with static systems, but is particularly well-suited for moving fluids.

Almost any fluid can be treated according to the process of the invention. The fluid should be essentially inert to the radiation being used. It is desirable, but not necessary, that the fluid be at least partially transparent to the radiation being transmitted. Water, and, in particular, water flowing through pipes or tubing, can be treated to advantage using the process of the invention. Other suitable fluids include organic solvents, aqueous and nonaqueous solutions, biotic fluids, either in vitro or in vivo, such as blood, aerosols, emulsions, dispersions, and gases such as air, nitrogen, etc.

Radiation-delivering fibers, frequently called "optical fibers" are well known as means for transmitting light and data. These fibers have historically been designed to transmit radiation with minimal radiation losses. Both glass and polymeric fibers can be used. In the process of the invention, the fibers may be of two different types: (1) fibers which transmit, emit and scatter radiation continuously along the length of the fiber, and (2) fibers which transmit radiation from one end of the fiber to the other with very little emission along the length. By "transmit," it is meant to transport radiation from one end of the fiber to the other. By "emit," it is meant to issue radiation circumferentially along the full length of the fiber.

The first type of radiation-delivering fiber, i.e., one which transmits, emits and scatters radiation continuously along the length of the fiber, is preferred. The fiber is constructed so that the radiation is emitted along the full length of the fiber with minimal absorption by the fiber itself or its cladding. If the fiber emits or absorbs too much radiation, less of the radiation will reach the end of the fiber. If the fiber emits or absorbs very little radiation, most of the radiation will be transmitted to the end, and the end of the fiber will act primarily as a point source. Thus the fiber should be partially transmitting and partially-emitting so that it acts as a radiation source along the full length of the fiber.

Materials which can be used for this type of radiation-delivering fiber include glasses and plastics which are essentially inert to the radiation being transmitted. Frequently, the fibers will have a core of one type of material and a cladding or shell of another type of material. The difference in the indices of refraction of the two materials can be chosen so as to balance the amount of internal reflection of the radiation, and thus transmission to the end of the fiber, and the amount of emission through the fiber and cladding. Alternatively, the material used to make the fiber may include scattering agents, and this, in conjunction with the selection of cladding material, may be used to control the relative amounts of transmission and emission of radiation along the fiber. Examples of glasses include silica-based glasses and those doped with various scattering agents, e.g., inorganic oxides. Examples of polymeric materials which may be used in practicing the invention include UV-resistant forms of homopolymers and copolymers of amides, acrylates, methacrylates, styrene, vinyl compounds, imides, fluoromonomers, sulfones, siloxanes, silicones, etheretherketones, etherketoneketones, ethylene, propylene, butadiene and related hydrocarbons, poly(perfluoroalkyl)methylmethacrylates and the like.

A single large fiber of this type or a multiplicity of smaller fibers can be used. The fibers may be cylindrical in shape or they may have different shapes adapted to suit the conduit or container used. The fibers may be arranged in different arrays including cylindrical bundles of fibers, flat or bent tapes, individual fibers independent of other fibers, etc. The exact size, geometry and number of fibers and the geometry of the array will be determined by the amount of radiation required, which is discussed below.

The second type of radiation-delivering fiber is one which primarily transmits the radiation with very little emission along the length of the fiber. When this type of fiber is used, a multiplicity of fibers is necessary. The fibers will be of varying lengths so that light is emitted at many points along the fluid path and approximates the type of emission obtained with the first preferred type of fiber. The individual fibers may have cylindrical or other geometry. The multiplicity of fibers can be arrayed in almost any geometrical configuration to suit the container or conduit being used. Examples of suitable arrays include cylindrical bundles of fibers, flat or bent tapes, individual fibers independent of other fibers, loose longitudinal or transverse arrays, woven or felted arrays, etc. Regardless of the particular geometry chosen, the ends of the fibers should be arranged so that the exposure to radiation of the fluid is maximized. It will be clear that the emitting fibers' ends are not all on one side of the array such that the non-emitting parts of the fibers shield parts of the fluid from the emitting ends.

The exact number of fibers and the difference in length between them will vary depending on the fluid conditions, i.e., the size of the fluid conduit or container, the level of contamination and desired level of purity for the fluid, the flow rate, etc. In general, good results are obtained when all the fluid in the conduit is exposed to sufficient radiation to insure a total kill of the microorganisms present. The radiation dosage levels which will accomplish a total kill for various microorganisms are known and vary from less than 2000 to more than 100,000 $\mu$W-sec.

Many different types of glass and polymeric materials can be used for this second type of fiber. Examples include glasses and plastics, or combinations thereof, which are essentially inert to the radiation being transmitted. Frequently the fibers will have a core of one type of material and a cladding or shell of another type of material. For this type of fiber, the difference between the indices of refraction of the two materials is chosen so as to maximize the amount of internal reflection of the radiation, and thus the transmission to the end of the fiber.

The radiation source can be any source which emits radiation of the desired wavelength. Ultraviolet radiation is generally defined as radiation having a wavelength from 10 to 390 nm. However, the most effective radiation for killing microorganisms and preventing microbial growth has a wavelength range of 100-300 nm. Suitable sources of this range of ultraviolet radiation include fluorescent, mercury vapor, mercury-xenon, metal additive, and arc lamps.

The intensity of the radiation source needed and the number of sources used will depend on the size of the container or conduit; the length, number and type of radiation-delivering fibers attached; the fluid flow rate; and the contamination level and desired purity level of the fluid. The radiation level necessary to destroy various types of microbial growth is well documented in the literature. The necessary intensity of the radiation source can then be calculated by standard methods based on the above noted factors, as, for example, in "UV Sterilization" by G. O. Schenk and *Handbook of Water Purification*, W. Lorch, ed. (McGraw-Hill Ltd., London 1981).

In most cases the radiation source will transmit radiation to the attached fibers, and hence to the fluid, in an uninterrupted fashion, i.e., in a continuous mode. This is the preferred mode. However, it is also possible for the radiation source to transmit radiation in a semi-continuous mode. In general, the semi-continuous mode will consist of short periods of radiation followed by short periods without radiation.

The radiation-delivering fiber(s) are connected to the radiation source in a transmitting relationship, i.e., they are connected in such a way so that nearly all of the radiation from the source is directed into the fibers. In general, this is accomplished by placing the fiber(s) into a fitting device. When a multiplicity of fibers is used, they are first gathered into a bundle and then placed in the fitting. The open end of the fitting is attached to a receiving aperture on the radiation source. The radiation from the source is directed through the aperture and thus to the fiber(s).

To carry out the process of the invention the fiber(s) must be arranged in such a way as to maximize the amount of the fluid that is exposed to radiation from the source at any one time. It is preferred that a major portion of the fluid be exposed to radiation at essentially the same time. By "major portion" it is meant at least 40% of the fluid volume; preferably 60% of the fluid volume; and most preferably 80% of the fluid volume. When the radiation source is in a continuous mode, a major portion of the fluid will be exposed to radiation at all times. When the radiation source is in a semi-continuous mode, a major portion of the fluid will be exposed to radiation during the pulses when the source is "on."

It is preferred that the fiber(s) be disposed internally with respect to the fluid. In most cases, the radiation source will be external to the fluid. The fiber(s) will be connected to the radiation source external to the fluid, pass into the fluid container through a leak-preventing opening port, and extend through the fluid as long as possible. In most cases it will be desirable to minimize the amount of fiber which is external to the fluid, since this part of the fiber serves little function. It is possible to prepare radiation-delivering fibers of great length, and therefore it is possible to use the process of the invention for pipes, tubes and conduits which are very long. It is also possible to pass the fiber(s) out of the fluid through a leak-preventing exit port to enable connection to radiation sources at both ends of the fiber(s). In this way, the radiation intensity can be increased.

It is also possible to place the radiation source directly in the fluid provided that it is properly protected from the fluid if contact with the fluid would be harmful to the source in any way. In this configuration, the source and the fiber(s) are all internal.

In a second embodiment, the process of the invention can be carried out using fiber(s) which are external to the fluid. In this embodiment, a single fiber or multiplicity of fibers is wrapped around the outside of the fluid container or conduit. In most cases, this embodiment will be used for fluid conduits, although it may be used for containers if the fluid is adequately agitated to bring all elements of the fluid volume to the walls of the container. It is clear that the conduit or container must have some transparency to the radiation so that the radiation will be transmitted through the wall of the conduit or container. One of two additional conditions must also be met: (1) the thickness or diameter of the fluid conduit or container must be very small so that every fluid volume element is exposed to radiation when passing through the conduit or held in the container; or (2) for larger-diameter conduits or containers, the fluid must be turbulent, so that every volume element is forced to the inner wall of the conduit or container for exposure to radiation.

The process of the invention is particularly advantageous when treating fluids of moderate to high opacity to ultraviolet radiation. In such cases the fluid can shield the microorganisms from killing radiation by absorbing that radiation. This is a particular difficulty with the processes of the prior art, as the exposure times, i.e., the amount of time any given element of fluid volume is exposed to radiation, are very short relative to the total residence time within the conduit. When treating fluids of moderate to high opacity, the microorganisms which are farthest from the radiation source at the time of contact with the source are generally shielded from the radiation by the intervening fluid. The process of the invention insures an increased and more even distribution of the radiation within the fluid so that all parts of the fluid will be exposed to radiation. This is especially true for moving fluids. The natural flow of the fluid causes different volume elements of the fluid to come in close contact with the fiber(s) all along the length of the conduit. It is preferred, for fluids of moderate to high opacity, to use a multiplicity of fibers in the conduit. The number, geometry and arrangement of the fibers can be designed so as to increase the turbulence of the fluid and to maximize the exposure of all parts of the fluid to the radiation.

EXAMPLES

Example 1

This example illustrates the effectiveness of the process of the invention in reducing the amount of microbial growth in a moving fluid using fibers which transmit radiation from one end of the fiber to the other with very little emission along the length.

The test chamber was a loop of tubing through which samples were continuously circulated to simulate a fluid conduit. The loop consisted of a straight portion for the irradiation and the additional tubing which was necessary to connect the system to a pump and complete the loop.

The straight section containing the optic fibers was a 36 cm section of straight Teflon ® FEP tubing with a Kynar ® tee at one end and a Kynar ® elbow at the other end. The loop was completed with 40 cm of C-Flex tubing onto which was mounted a peristaltic pump. The tubing was all ⅜ inch (0.95 cm) outer diameter and ¼ inch (0.64 cm) inner diameter. The fluid went from the pump head to C-Flex tubing, to the tee, through the Teflon ® FEP tubing, to the elbow, to C-Flex tubing back to the pump, at a rate of 5 ml/minute.

The fiber bundle consisting of 48 individual fibers (Northern Lights Cable, North Bennington, Vt.) was inserted into the Teflon ® FEP tubing through the Kynar ® elbow. The fibers had the following lengths in cm: 6.4, 7.5, 8.8, 10.7, 11.4, 12.5, 14.8, 16.5, 18.5, 21.3, 22.7, 25.4, 28.0, 29.2, 29.4 and 30.7. The first 6 cm of the fiber bundle was left outside of the tubing for connection to a 100 W UV source. When the UV source was powered and the fibers connected, there was approximately 100 $\mu$W of UV radiation at the end of each fiber, and approximately 3-7 $\mu$W of UV radiation emitted along the length of the fibers.

Prior to running each sample through the loop, the loop containing the fiber bundle was treated to remove any microbial contamination using the following procedure: the loop was treated with 5 ppm hypochlorite in deionized water for 20 minutes, and followed by a 20 minute treatment using 0.5 ml of a 10% solution of sodium thiosulfate added to the chlorinated water, followed by flushing with deionized water.

The fluid to be tested was water containing 100,000 *Escherichia coli* per ml. *Escherichia coli* was chosen as it is the primary indicator organism of sanitary significance.

To conduct a test, samples of the water were admitted to the loop. The samples were circulated in the loop for the times given below. For the Example the ultraviolet lamp was connected to the fibers for the entire time the samples were circulating. For the Control the lamp was disconnected from the fibers so that the sample saw no radiation during the circulation. Test fluids were removed from the loop after the designated time period, and placed into sterile containers. The surviving concentration of *Escherichia coli* was determined by serially diluting the test fluid in Standard Methods phosphate buffer (APHA), plating in duplicate using MacConkey Agar, and incubating at 35° C. for 48 hours. Colonies with a surrounding pink precipitate were read as *Escherichia coli.* Each test was repeated four times for both the irradiated and nonirradiated samples. The results are given in the table below.

| Time (minutes) | *Escherichia coli* (ppm) | |
| --- | --- | --- |
| | Example | Control |
| 3 | 33,000 | 150,000 |
| 10 | 1,800 | 110,000 |
| 15 | 1,200 | 150,000 |

Example 2

This example illustrates the process of the invention using radiation-delivering fibers which transmit, emit and scatter radiation continuously along the length of the fiber.

The test conduit is a PVC pipe of length equivalent to the full length of the conduit in Example 1 (76 cm) and of the same internal diameter with entrance and exit ports at opposite ends. Into the pipe are inserted 48 optical fibers which are loose, i.e., not in a bundle. The fibers have a core and shell made of glass doped with scattering agents. The difference between the indices of refraction of the core and the shell is such that there is some internal reflection and some transmission along the length of the fiber. The fibers are approximately 92 cm in length. The first and last 6 cm of each fiber are left outside of the pipe for connection to a 100 W UV source at each end. The fibers are connected to the UV sources as described in Example 1. When the UV sources are powered and the fibers connected, there is approximately 15-20 μW of UV radiation emitted along the length of the fibers.

Prior to admitting the test fluid, the pipe is treated to remove any microbial contamination as described in Example 1. The fluid tested is the same as that in Example 1 with a once-through flow rate equal to that in Example 1, 5 ml/minute. Samples of fluid are taken from the exit port and analyzed for the surviving concentration of *Escherichia coli* as described in Example 1. It is found that the concentration of *Escherichia coli* is reduced to a substantially greater extent.

Example 3

This example illustrates the process of the invention using radiation-delivering fibers which transmit, emit and scatter radiation continuously along the length of the fiber, and which are located external to the fluid to be treated.

Forty-eight optic fibers as described in Example 2 are wrapped around the outer surface of 76 cm length of glass tubing having an inner diameter of ¼ inch (0.64 cm). The fibers are wrapped around the tubing in a helical manner with the fibers in contact but with as little overlap as possible. The fibers are attached to a 100 W UV source at each end as in Example 2. The fiber-wrapped tubing is ensheathed by a conforming sheath which has a refractive index appropriate to reflect UV radiation impinging on its inner diameter into the underlying fibers and tubing. The tubing is initially treated to remove microbial contamination as in Example 1. The fluid tested is the same as that in Example 2 with the same once-through flow rate, 5 ml/minute, and exposure time as in Example 2.

Samples of the fluid exiting the tubing are taken and analyzed for the concentration of *Escherichia coli* as described in Example 1. It is found that the concentration of *Escherichia coli* is very low, but higher than in Example 2.

What is claimed is:

1. A process for treating a fluid with ultraviolet radiation which comprises exposing the fluid to ultraviolet radiation, while said fluid is held in a conduit or container, said exposure being accomplished by means of
   a multiplicity of radiation-delivering fibers having first and second ends, said first ends disposed within said fluid, said fibers having varying lengths and emitting radiation substantially only at the first ends thereof, said lengths being selected to ensure that the fluid in the conduit or container is exposed to sufficient radiation to ensure a satisfactory level of destruction of microorganisms in said fluid, said second ends of said fibers being connected in a transmitting relationship with
   a radiation source.

2. The process of claim 1 wherein a major portion of the fluid is exposed to radiation from the source at essentially the same time.

3. The process of claim 1 wherein the radiation source is in a continuous mode.

4. The process of claim 1 wherein the radiation source is in a semi-continuous mode.

5. The process of claim 1 wherein the radiation source is disposed externally with respect to the fluid.

6. The process of claim 1 wherein the radiation source is disposed internally with respect to the fluid.

7. The process of claim 1 wherein the radiation-delivering fiber comprises UV-stable polymeric material selected from the group consisting of homopolymers and copolymers of amides, acrylates, methacrylates, styrene, vinyl compounds, imides, fluoromonomers, sulfones, siloxanes, silicones, etheretherketones, etherketoneketones, ethylene, propylene and butadiene.

8. The process of claim 1 wherein the radiation-delivering fiber is selected from the group consisting of glass, quartz and glasses containing scattering agents.

9. The process of claim 1 wherein the fluid is water.

10. The process of claim 1 wherein the fluid contains biotic UV absorbing components.

11. The process of claim 1 wherein the fluid is a non-aqueous liquid.

12. The process of claim 1 wherein the fluid is a gas.

13. The process of claim 1 wherein the fluid is an aerosol.

14. The process of claim 1 wherein the fluid is an emulsion.

15. The process of claim 1 wherein the fluid is a dispersion.

* * * * *